(12) United States Patent
Goldstein et al.

(10) Patent No.: US 11,213,250 B2
(45) Date of Patent: Jan. 4, 2022

(54) APPARATUS AND METHOD FOR CONDUCTING ELECTROENCEPHALOGRAPHY

(71) Applicant: Memory MD, Inc., New York, NY (US)

(72) Inventors: Boris Goldstein, New York, NY (US); Dmitriy Prilutskiy, Moscow (RU); Stanislav Zabodaev, Solnechnogorsk (RU)

(73) Assignee: Memory MD, Inc., New York, NY (US)

( * ) Notice: Subject to any disclaimer, the term of this patent is extended or adjusted under 35 U.S.C. 154(b) by 876 days.

(21) Appl. No.: 15/898,611

(22) Filed: Feb. 18, 2018

(65) Prior Publication Data

US 2018/0235541 A1   Aug. 23, 2018

Related U.S. Application Data

(60) Provisional application No. 62/462,282, filed on Feb. 22, 2017.

(51) Int. Cl.
*A61B 5/00* (2006.01)
*A61B 5/291* (2021.01)
*A61B 5/369* (2021.01)
*A61B 5/316* (2021.01)

(52) U.S. Cl.
CPC ............ *A61B 5/6803* (2013.01); *A61B 5/291* (2021.01); *A61B 5/369* (2021.01); *A61B 5/316* (2021.01); *A61B 5/6814* (2013.01); *A61B 5/6843* (2013.01)

(58) Field of Classification Search
None
See application file for complete search history.

(56) References Cited

U.S. PATENT DOCUMENTS

| | | | |
|---|---|---|---|
| 2010/0125190 A1 | 5/2010 | Fadem | |
| 2010/0274152 A1* | 10/2010 | McPeck | A61B 5/291 600/544 |
| 2012/0143020 A1* | 6/2012 | Bordoley | A61B 5/291 600/301 |
| 2013/0172721 A1 | 7/2013 | McPeck et al. | |

(Continued)

FOREIGN PATENT DOCUMENTS

WO   2014145487 A1   9/2014

OTHER PUBLICATIONS

International Preliminary Report on Patentability of corresponding application No. PCT/US2018/018570; dated Aug. 27, 2019; 8 pages.

(Continued)

*Primary Examiner* — Thomas S McCormack
(74) *Attorney, Agent, or Firm* — Young Basile Hanlon & MacFarlane, P.C.

(57) ABSTRACT

A disposable apparatus for electroencephalography measurement on a human subject is provided. The disposable apparatus for electroencephalography measurement may be securely attached to the subject's head without attachment gel contacting the subject' scalp. A transparent body is provided for easy placement of electrodes. Methods to use the apparatus for electroencephalography measurement are also provided.

16 Claims, 6 Drawing Sheets

(56) References Cited

U.S. PATENT DOCUMENTS

| | | | |
|---|---|---|---|
| 2015/0011857 A1* | 1/2015 | Henson | A61B 5/6831 |
| | | | 600/383 |
| 2015/0257674 A1 | 9/2015 | Jordan et al. | |
| 2015/0282760 A1 | 10/2015 | Badower et al. | |
| 2018/0165566 A1* | 6/2018 | Rogers | G01J 5/10 |

OTHER PUBLICATIONS

International Search Report of corresponding application No. PCT/US2018/018570; dated Apr. 23, 2018; 2 pages.
Search report from corresponding European patent application EP 18757492; dated Sep. 3, 2020; 1 page.

\* cited by examiner

APPARATUS AND METHOD FOR CONDUCTING ELECTROENCEPHALOGRAPHY

CROSS-REFERENCE TO RELATED APPLICATIONS

This application claims the benefit of U.S. Provisional Application No. 62/462,282, filed Feb. 22, 2017. Each of the above-referenced patent applications is incorporated by reference in its entirety.

BACKGROUND OF THE INVENTION

Field of the Invention

This invention relates to an apparatus used in electroencephalography and a method to perform electroencephalography using this apparatus. The apparatus is disposable and may be applied to a human subject's head in many settings.

Description of the Related Technology

Electroencephalography (EEG) is the recording of electrical signals along the scalp. Brains' neural activities generate electrical voltage fluctuations, whose signals may be measured by EEG. EEG measurements are useful for medical diagnosis and behavioral therapy. Other medical techniques involving the recording of bio-potential signals are electrocardiograms (ECG) and electromyograms (EMG).

Electroencephalography is particularly useful in diagnosis of conditions relating to brain injuries, such as seizure, stroke, brain tumors, Alzheimer's disease, or certain psychoses. Neural activities generate bio-potentials, which are collected by electrodes situated by a cap or by application of each electrode on certain head regions and conducted through electrical connections to a process hub.

EEG measurements typically require application of electrodes to the subject's head by either a cap application or placement of each electrode. Placement of each electrode is time consuming and requires a trained technician. Moreover, reusable caps and electrodes require cleaning and adding of gel, which may be time consuming and a means for germ transmission.

SUMMARY

According to embodiments of the present invention, there is provided an apparatus for performing electroencephalography on a human subject. The apparatus comprises a mid sheet extending from the forehead anchor to the connector point; a frontal portion with a front left wing and a front right wing extending from the mid sheet at the forehead anchor to the left and right, respectively; a coronal portion with a coronal left side wing and a coronal right side wing extending from the middle of the mid sheet to the left and right, respectively; a lateral portion with a rear left side wing and a right left side wing extending from the rear of the mid sheet, respectively; a plurality of circuitry connecting a plurality of electrodes to a connector point situated at the end of the mid sheet. On the apparatus are electrodes situated at positions $F_z$, $C_z$, $P_z$, $F_7$, $F_{p1}$, $F_8$, $F_{p2}$, $C_3$, $T_3$, $A_1$, $C_4$, $T_4$, $A_2$, $T_5$, $O_1$, $T_6$, and $O_2$.

There is provided an apparatus for conducting electroencephalography, the apparatus comprising:
 a mid sheet extending from the forehead anchor to the connector point, comprising a plurality of embedded electrodes at positions $F_z$, $C_z$ and $P_z$ of the International Standard 10-20 System for electrode placement and a ground electrode;
 a frontal portion comprising:
  a front left wing extending from the mid sheet at the forehead anchor at an angle and comprising a plurality of embedded electrodes at positions $F_7$ and $F_{p1}$ of the International Standard 10-20 System for electrode placement and an attachment point at the distal end;
  a front right wing extending from the mid sheet at the forehead anchor at an angle and in the opposite direction of the front left wing, comprising a plurality of embedded electrodes at positions $F_8$ and $F_{p2}$ of the International Standard 10-20 System for electrode placement and an attachment point at the distal end;
  a forehead anchor between the front left wing and the front right wing; and
 a coronal portion comprising:
  a coronal left side wing extending from the middle of the mid sheet at an angle and comprising a body and two extensions, a first extension extending from the body to one side at an angle less than 90 degrees taken between the body and the first extension in the clockwise position, a second extension extending from the body to the opposite side at an angle less than 90 degrees taken between the body and the second extension in the anti-clockwise position, with embedded electrodes at positions $C_3$ and $T_3$ in the body, and an embedded electrode at position $A_1$ on the first extension, the electrode positions are according to the International Standard 10-20 System for electrode placement, and an attachment point at the distal end of the body;
  a coronal right side wing extending from the middle of the mid sheet at an angle and in the opposite direction of the front left wing, comprising a body and two extensions, a first extension extending from the body to one side at an angle less than 90 degrees taken between the body and the first extension in the clockwise position, and a second extension extending from the body to the opposite side at an angle less than 90 degrees taken between the body and the second extension in the anti-clockwise position, with embedded electrodes at positions $C_4$ and $T_4$ in the body, and an embedded electrode at position $A_2$ on the second extension, the electrode positions are according to the International Standard 10-20 System for electrode placement, and an attachment point at the distal end of the body;
 a lateral portion comprising:
  a rear left side wing extending at an angle from the rear end of the mid sheet comprising a plurality of embedded electrodes at positions $T_5$ and $O_1$ of the International Standard 10-20 System for electrode placement and an attachment point at the distal end of the rear left wing;
  a rear right side wing extending at an opposing angle from the mid sheet comprising a plurality of embedded electrodes at positions $T_6$ and $O_2$ of the International Standard 10-20 System for electrode placement and an attachment point at the distal end of the rear right wing; and
 a plurality of circuitry connecting the plurality of electrodes to a common connector point situated at the end of the mid sheet, wherein the mid sheet ends at a connector point with embedded circuitry, wherein the mid sheet, the frontal portion, the coronal portion, and the lateral portion comprise the apparatus body, and wherein the apparatus body comprises a base layer.

There is provided an EEG apparatus for EEG measurement as above and the EEG apparatus may have a transparent or seen-through base layer.

There is provided an EEG apparatus for EEG measurement as above and the circuitry in the EEG apparatus may be imprinted and made of silver and/or silver chloride.

There is provided an EEG apparatus for EEG measurement as above and the electrodes within the EEG apparatus may be imprinted and made of silver and/or silver chloride.

There is provided an EEG apparatus for EEG measurement as above and the circuitry and electrodes may be printed in one stage.

There is provided an EEG apparatus for EEG measurement as above and the plurality of electrodes may extend from the apparatus and expose outside the base layer and with a conductive gel layer present on the base layer.

There is provided an EEG apparatus for EEG measurement as above and the plurality of electrodes may have sponges covering the conductive gel layer, and the sponges may be soaked with conductive gel.

There is provided an EEG apparatus for EEG measurement as above and the apparatus further comprises a holder in which the apparatus is placed.

There is provided an EEG apparatus for EEG measurement as above and the attachment points comprise gel spots covered by a thin film.

There is provided an EEG apparatus for EEG measurement as above and the attachment points comprise Velcro surfaces.

Further, there is provided a method for conducting electroencephalograph using the above provided apparatus, the method comprising:

providing an apparatus for performing electroencephalography on a human subject, the apparatus comprising:

a mid sheet extending from the forehead anchor to the connector point, comprising a plurality of embedded electrodes at positions $F_z$, $C_z$ and $P_z$ of the International Standard 10-20 System for electrode placement and a ground electrode;

a frontal portion comprising:

a front left wing extending from the mid sheet at the forehead anchor at an angle and comprising a plurality of embedded electrodes at positions $F_7$ and $F_{p1}$ of the International Standard 10-20 System for electrode placement and an attachment point at the distal end;

a front right wing extending from the mid sheet at the forehead anchor at an angle and in the opposite direction of the front left wing, comprising a plurality of embedded electrodes at positions $F_8$ and $F_{p2}$ of the International Standard 10-20 System for electrode placement and an attachment point at the distal end;

a forehead anchor between the front left wing and the front right wing; and a coronal portion comprising:

a coronal left side wing extending from the middle of the mid sheet at an angle and comprising a body and two extensions, a first extension extending from the body to one side at an angle less than 90 degrees taken between the body and the first extension in the clockwise position, a second extension extending from the body to the opposite side at an angle less than 90 degrees taken between the body and the second extension in the anti-clockwise position, with embedded electrodes at positions $C_3$ and $T_3$ in the body, and an embedded electrode at position $A_1$ on the first extension, the electrode positions are according to the International Standard 10-20 System for electrode placement, and an attachment point at the distal end of the body;

a coronal right side wing extending from the middle of the mid sheet at an angle and in the opposite direction of the front left wing, comprising a body and two extensions, a first extension extending from the body to one side at an angle less than 90 degrees taken between the body and the first extension in the clockwise position, and a second extension extending from the body to the opposite side at an angle less than 90 degrees taken between the body and the second extension in the anti-clockwise position, with embedded electrodes at positions $C_4$ and $T_4$ in the body, and an embedded electrode at position $A_2$ on the second extension, the electrode positions are according to the International Standard 10-20 System for electrode placement, and an attachment point at the distal end of the body;

a lateral portion comprising:

a rear left side wing extending at an angle from the rear end of the mid sheet comprising a plurality of embedded electrodes at positions $T_5$ and $O_1$ of the International Standard 10-20 System for electrode placement and an attachment point at the distal end of the rear left wing;

a rear right side wing extending at an opposing angle from the mid sheet comprising a plurality of embedded electrodes at positions $T_6$ and $O_2$ of the International Standard 10-20 System for electrode placement and an attachment point at the distal end of the rear right wing; and a plurality of circuitry connecting the plurality of electrodes to a common connector point situated at the end of the mid sheet, wherein the mid sheet ends at a connector point with embedded circuitry, wherein the mid sheet, the frontal portion, the coronal portion, and the lateral portion comprise the apparatus body, and wherein the apparatus body comprises a base layer;

affixing the apparatus to the patient by affixing the frontal portion to the forehead of the patient, affixing the front portion of the mid sheet from the forehead anchor to the junction between the mid sheet and the coronal elements along the sagittal line of the patient's head, affixing the coronal elements along the coronal line of the human subject's head, affixing the extensions around the left ear and right ear of the patient, securing the front left and right wings to the coronal attachment points, affixing the middle part of the mid sheet from the $C_z$ location to the junction between lateral portion and mid sheet along the sagittal line of the human subject's head, affixing the lateral portion to the human subject's scalp and securing the rear left and right wings to the coronal attachment points, affixing the rear portion of the mid sheet to the patient's scalp; and connecting the connector point to an electroencephalography cable, wherein affixing the apparatus further comprises contacting the conductive gel to adhere the electrodes to the human subject's scalp.

There is also provided a method to diagnose a neurological condition or disease, the method comprises:

selecting a subject potentially having a neurological condition or disease; and performing electroencephalography on the subject using an electroencephalography apparatus as in a method above to produce an electroencephalogram.

There is provided a method above, further comprising diagnosing the neurological condition or disease by interpreting the electroencephalogram There is provided a method above, further comprising treating the neurological condition or disease diagnosed, and the neurological condition or disease is epilepsy or a stroke.

ABBREVIATIONS

EEG: Electroencephalography
DIN: Deutsches Institut Für Normung
EMG: Electromyograms

DETAILED DESCRIPTION OF CERTAIN INVENTIVE EMBODIMENTS

As used herein, the word "wiredly" means a connection by physical means, such as by a continuous body of metal or conductive material.

As used herein, the word "attachment point" means a point at which an attachment means is located and capable of attaching to another physical object.

As used herein, the International Standard electrode placement system, or the 10-20 system refers to the International 10-20 system to describe and apply the location of scalp electrodes in the context of an EEG test or experiment.

As used herein, the directional term "left" refers to the left side of the human subject upon which this EEG apparatus is affixed. The directional term "right" refers to the right side of the human subject upon which this EEG apparatus is affixed.

Figure 6:
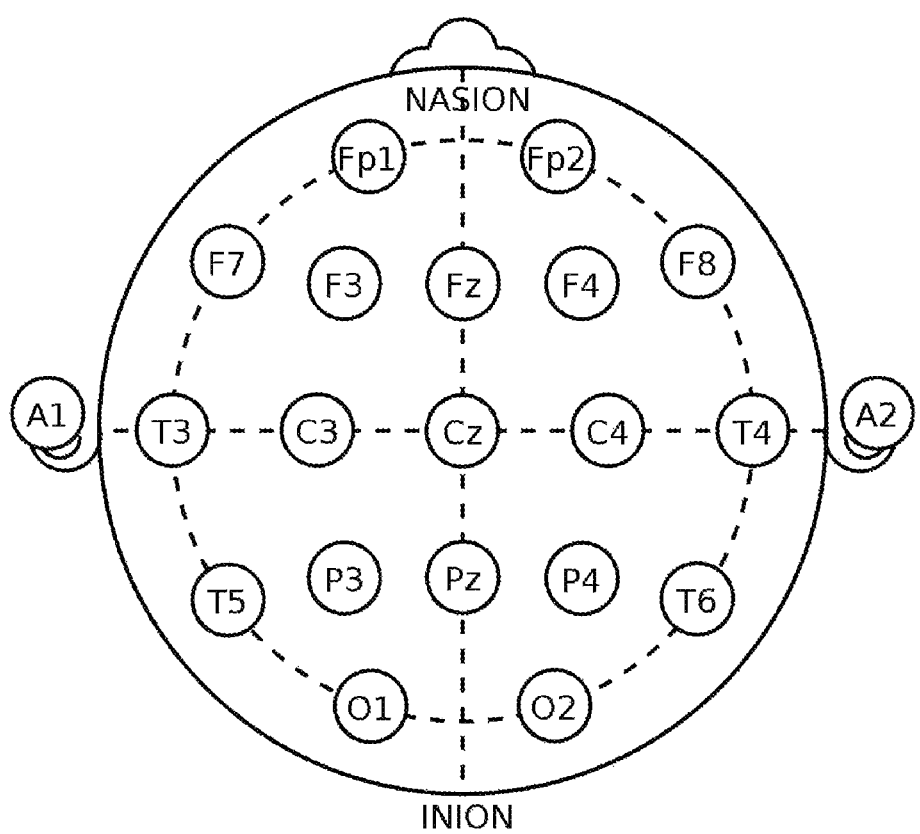
FIG. 6 illustrates the International Standard electrode placement system.

The terms "International Standard electrode placement system", "International Standard 10-20 electrode placement system", and "International Standard 10-20 System" are used interchangeably and refer to the International Standard 10-20 electrode placement system, which is illustrated in FIG. 6.

The terms "human subject" and "subject" are used interchangeably to refer to a human whose head is affixed with the EEG apparatus herein during use.

All dimensions specified in this specification are by way of example only and not intended to be limiting. Drawings are not necessarily drawn to scale. The actual size of the EEG apparatus herein may be chosen or modified for intended use, including use in adults with different head sizes, in children and/or infants. The actual size may also be tailored to the specific human subject who may use this EEG apparatus. Generally, the EEG apparatus herein has three sizes: large, medium, and small. Other sizes and dimensions are contemplated.

The EEG apparatus disclosed herein and its components may be made by any suitable material for the intended purpose of the electroencephalography apparatus. Specific materials may be discussed herein but only for illustration purposed only, and will not be understood as limiting in anyway.

The EEG apparatus herein provides EEG channels to collect the patient's brain signal and thereafter brain activity may be interpreted, such that any conditions can be identified and treated, if necessary. This EEG apparatus may be disposable, such that it can be discarded after each use, therefore preventing accumulation of microbials on EEG apparatuses. The EEG apparatus disclosed herein may be easily stored and transported and therefore is suitable for use both in clinic settings and at non-clinical settings, such as in battlefields or accident scenes. The EEG apparatus may be used for medical treatment and research purposes or other purposes, such as training and sleep studies. Other uses may be possible, depending on the need determined by the users.

Embodiments of this application relate to a disposable EEG apparatus embedded with electrodes for use in electroencephalography. The apparatus may be generally transparent or seen-through for ease of application and connection. All electrodes may be wiredly connected to a main outlet connector, which is connected to an outside processor. The EEG apparatus may utilize the International Standard 10-20 electrode positioning system and including at least one ground electrode and at least one reference electrode. The locations and number of electrodes on the EEG apparatus may be chosen to ensure adequate recording of EEG signal.

The EEG apparatus may provide adequate electrodes to channel brain neural activities as detected in a human subject, thereby facilitating interpretation of the EEG signal. The EEG apparatus according to embodiments herein may be easily applied and disposed of after one use. Flat electrodes embedded into EEG the apparatus may provide increased comfort to human subjects. Applications for the EEG apparatus may include neural brain measurement in clinical settings or in field settings such as in battlefields or accident scenes.

Figure 1:
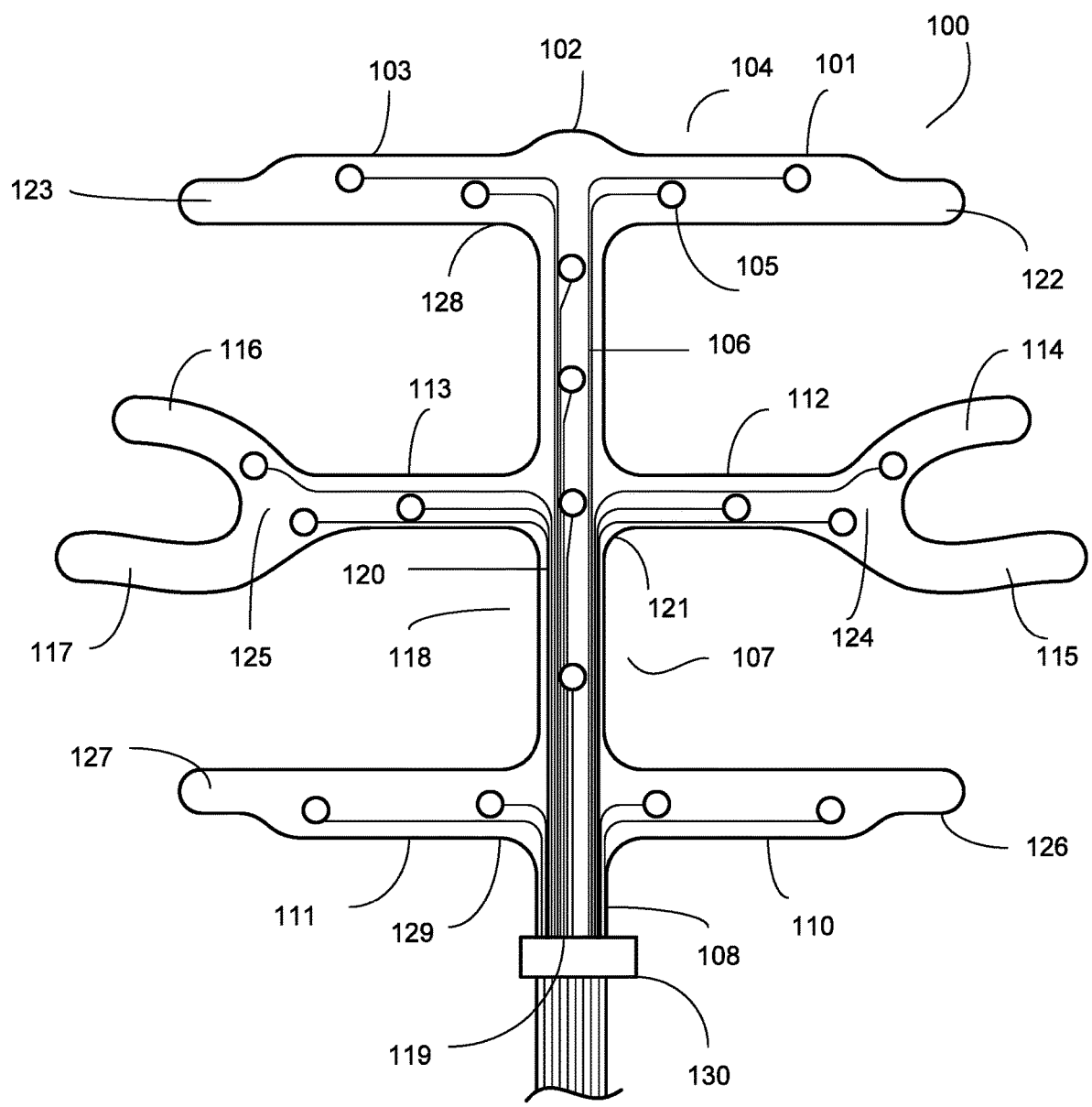
FIG. 1 depicts the top view of the EEG apparatus according to embodiments.

According to embodiments of this invention, there is provided an EEG apparatus 100 comprising a frontal portion 128, a coronal portion 121, and a lateral portion 129 integrally connected by a mid sheet 118. The mid sheet 118 may comprise the front portion 106, the middle portion 107, and the read portion, 108. The EEG apparatus 100 is depicted in FIG. 1. The EEG apparatus 100 may be made of elastic and pliable materials to allow for proper positioning on the human subject's head. This material may also provide electrical insulation for electrodes and wires and/or connection inside. The EEG apparatus 100 may be transparent or clear, allowing electrodes to be seen, which may facilitate proper positioning.

The frontal portion 128 of the EEG apparatus 100 may comprise a forehead anchor 102 positioned as an extension towards the front of the mid sheet 118 of the EEG apparatus 100 and two opposing left front wing 103 and right front wing 101 forming the forehead wing. The mid sheet 118 of the EEG apparatus 100 may be shaped as a straight, narrow sheet extending from the base of the skull to the middle of the forehead of the human subject upon application, with wings extending from the front 106, the middle 107, and the rear of portion the mid sheet 108. The coronal portion 121 may comprise the coronal right and left wings 112, 113 and the middle part of mid sheet 107. The lateral portion 129 of the EEG apparatus 100 may comprise the rear part of the mid sheet 108 and the two (2) rear side wings 110, 111.

The frontal portion 104 may comprise a forehead anchor 102, which may improve placement of the EEG apparatus 100 on the human subject. The forehead anchor 102 may be affixed to the subject's forehead during use. The lower surface of the forehead anchor 102 may have a layer of attachment gel covered by another layer of plastic and/or paper. The frontal portion 104 may comprise two (2) wings, with the front left wing 103 extending from the left side of the front mid sheet 106 at the forehead anchor and the front right wing 101 extending from the right side of the front mid sheet 106. Positioned on the front left wing 103 may be a plurality of electrodes, which may be two (2) electrodes at positions $F_{p1}$ and $F_7$ of the International Standard 10-20 System. Electrodes are connected by imprinted circuitry 120, 207 and routed to the connector point 119. Positioned on the front right wing 101 may be a plurality of electrodes, which may be two (2) electrodes at position $F_{p2}$ and $F_8$ of the International Standard 10-20 System, which are also connected by imprinted circuitry 120, 207. Electrode positions are confirmed upon application to the subject's scalp. The front part of mid sheet 106 extends from the forehead anchor 102 towards the coronal portion 121.

At the distal end of each of the front left and right wing 103, 101 may be a frontal attachment point 122, 123. The frontal attachment points 122, 123 may comprise an attachment gel spot covered by a thin film, which may be peeled off for attachment to the attachment points on the coronal left and right side wings 125, 124. Alternatively, the frontal attachment points 122, 123 may comprise a Velcro—like attachment mechanism to mate with a corresponding Velcro surface at the attachment points on the coronal left and right side wings 125, 124, or other attachment means.

The front part of the mid sheet 106 may extend from the middle of the forehead wing 104 at the forehead anchor 102 towards the base of the neck along the sagittal line. The front part of the mid sheet 106 may have an electrode situated at position $F_z$ according to the International Standard 10-20 System and a ground electrode.

At approximately the middle of the mid sheet 118, corresponding to the top of the subject's head at the coronal line may be a coronal portion 121 with two coronal side wings 112, 113. The coronal left side wing 113, upon application to the subject's head, may extend from the subject's top of the head to the subject's left ear. The coronal right side wing 112, upon application to the subject's head, may extend from the subject's top of the head to the subject's right ear.

On each of the coronal left and right side wing 113, 112, above the point at which extensions extend from each of the left and right side wing 113, 112 may be an attachment point 124, 125. The attachment points 124, 125 may mate with the front attachment points 123, 122 to secure the EEG apparatus 100 in place. The attachment points 124, 125 may be a flat surface on which attachment gel from the front attachment points 123, 122 may be applied, or may be a Velcro surface to mate with another Velcro surface present on the front attachment points 122, 123.

Positioned on the coronal left side wing 113 may be a plurality of electrodes, which may be two (2) electrodes at positions $C_3$ and $T_3$ in the International Standard 10-20 System. The coronal left side wing 113 may comprise an extending body which may branch into two (2) extensions 116, 117. The angle at which the first extension 116 may extend from the extending body may be less than 90 degrees taken between the extending body and the first extension in clockwise position. The angle at which the second extension 117 may extend from the extending body may be less than 90 degrees taken between the extending body and the second extension in anti-clockwise position. An embedded electrode may be situated at position $A_1$ on the first extension 116 and may act as the reference electrode. The lower surface of each of the two extensions 116, 117 may be a layer of attachment gel covered by a thin film.

Positioned on the coronal right side wing 112, which extends from the middle portion of the mid sheet 107 to an opposing side of the coronal left side wing, may be a plurality of electrodes, which may be two (2) electrodes at positions $C_4$ and $T_4$ in the International Standard 10-20 System. The coronal right side wing 112 may comprise an extending body which may branch into two (2) extensions 114, 115. The angle at which the first extension 115 may extend from the extending body may be less than 90 degrees taken between the extending body and the first extensions in clockwise position. The angle at which the second extension 114 may extend from the extending body may be less than 90 degrees taken between the extending body and the second extension in anti-clockwise position. An electrode may be situated at position $A_2$ according to the International Standard 10-20 System for electrode placement on the second extension 114 and may act as a reference electrode.

The lower surface of each of the two extensions 114, 115 on the coronal right wing may be a layer of attachment gel covered by a thin film. The middle part of the mid sheet 107 may extend backward from the middle of the coronal portion 121 to the back of the subject's head. The middle part of the mid sheet 107 may comprise a plurality of electrodes, which may be two (2) electrodes at positions $P_z$ and $C_z$ in the International Standard 10-20 System for electrode placement.

The lateral portion 129 of the EEG apparatus may comprise the rear portion of the mid sheet 108 and two opposing rear wings 110, 111. The rear left side wing 111 may extend from the mid sheet 118 at an angle which may be approximately perpendicular to the mid sheet 118 and to the left of the mid sheet 118, but other angles are contemplated. Positioned on the rear left side wing 111 may be a plurality of electrodes, which may be two (2) electrodes at positions $T_5$ and $O_1$ in the International Standard 10-20 System. The rear right side wing 110 may extend from the mid sheet 118 at an angle which may be approximately perpendicular to the mid sheet 118 and to the right of the mid sheet 118, but other angles are contemplated. Positioned on the right side rear wing 110 may be a plurality of electrodes, which may be two (2) electrodes at position $T_6$ and $O_2$ in the International Standard 10-20 System.

At the distal end of each of the rear left and right wing 110, 111 may be a rear attachment point 126, 127. The rear attachment points 126, 127 may comprise an attachment gel spot covered by a thin film, which may be peeled off for attachment to the attachment point on the coronal left and right side wings 124, 125, or on the frontal attachment points 123, 122 on the frontal left 103 and right wing 101. Alternatively, the rear attachment points 126, 127 may comprise a Velcro—like attachment mechanism to mate with a corresponding Velcro surface on the coronal left and right side wings 124, 125, or to mate with a corresponding Velcro surface attachment points on the front left and right side wings 123, 122. Other attachment means are contemplated.

The mid sheet 118, upon affixing to the subject's head, may extend towards the subject's neck and end in a connector point 119 forming the rear portion of the mid sheet 108, and together with the rear left wing 110 and rear right wing 111, may form the lateral portion 129. The mid sheet 118 may have embedded circuitry 120, which may end at the bottom of the mid sheet 118 at the connector point 119. The total length of the mid sheet 118 may be 30-70 cm. Other lengths are contemplated.

Electrodes 105 may be present on the EEG apparatus 100 at specified locations in the International Standard 10-20 System. The locations shown in FIG. 1 and discussed specifically herein are exemplary only. Other electrode locations may be contemplated in embodiments. Electrodes may be connected by circuitry 120, which are ultimately connected to the connector 119.

Figure 2:
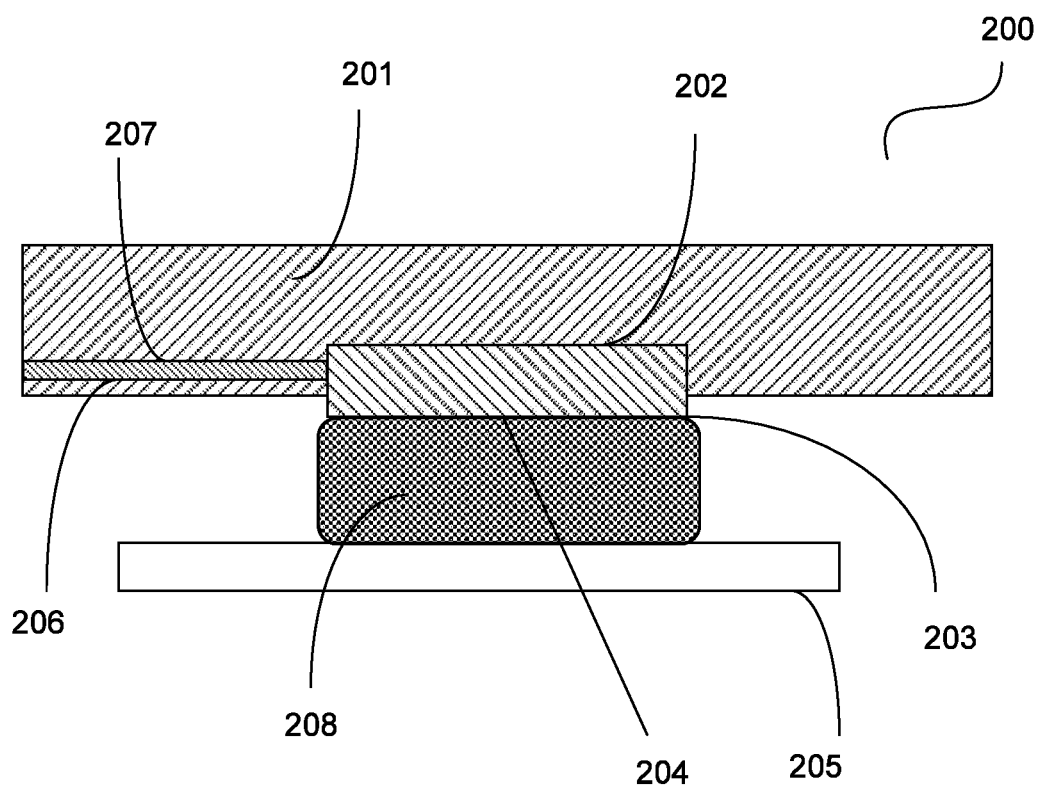
FIG. 2 depicts the cross sectional view of the EEG apparatus at a point where an electrode is present.

The cross section of the EEG apparatus at an electrode in an exemplary embodiment of the invention may be depicted in FIG. 2. The EEG apparatus 100 according to embodiments may comprise a base layer 201, which may provide structural support for the EEG apparatus 100. The base layer may be 0.1-0.3 mm, preferably 0.125 mm, in thickness, and 15-45 mm in width. Suitable materials for the EEG apparatus 100 base layer 201 may be polycarbonate plastic or polyester. The base layer 201 may be transparent or seen-through material for proper placement of the electrodes. Circuitry 207 may be embedded into the base layer 201 by printing. Electrodes 202 may be placed at certain positions corresponding to electrode positions in the International Standard 10-20 System. Electrodes 202 may be in electrical contact with circuitry 207 by printing. Electrodes 202 may be integrated with circuitry 207 by one-stage printing using the same material.

Circuitry 207 may be included in the EEG apparatus 100. Circuitry may be imprinted, such as by silver or silver—silver chloride composition, or may be wire embedded into the EEG apparatus 100. Other materials for the circuitry are contemplated. Circuitry 207 thickness may be 0.005-0.030 mm, preferably at 0.015 mm. A plurality of electrodes 202 may be positioned on the EEG apparatus 100, such that each electrode may be in contact with and conductively connected to the circuitry 207. All circuitry may be routed and may end at a connector point 119, where a plug or outside connector may be connected to transmit collected signals to a processor. The connector 119 is configured to mate with corresponding outside connectors, which may be connected to a standard EEG recording system.

Circuitry 207 may be covered by a dielectric layer for insulation, in addition to the base layer. The dielectric layer may be a polymer composition. Other suitable materials for the dielectric layer may be used.

Figure 5:
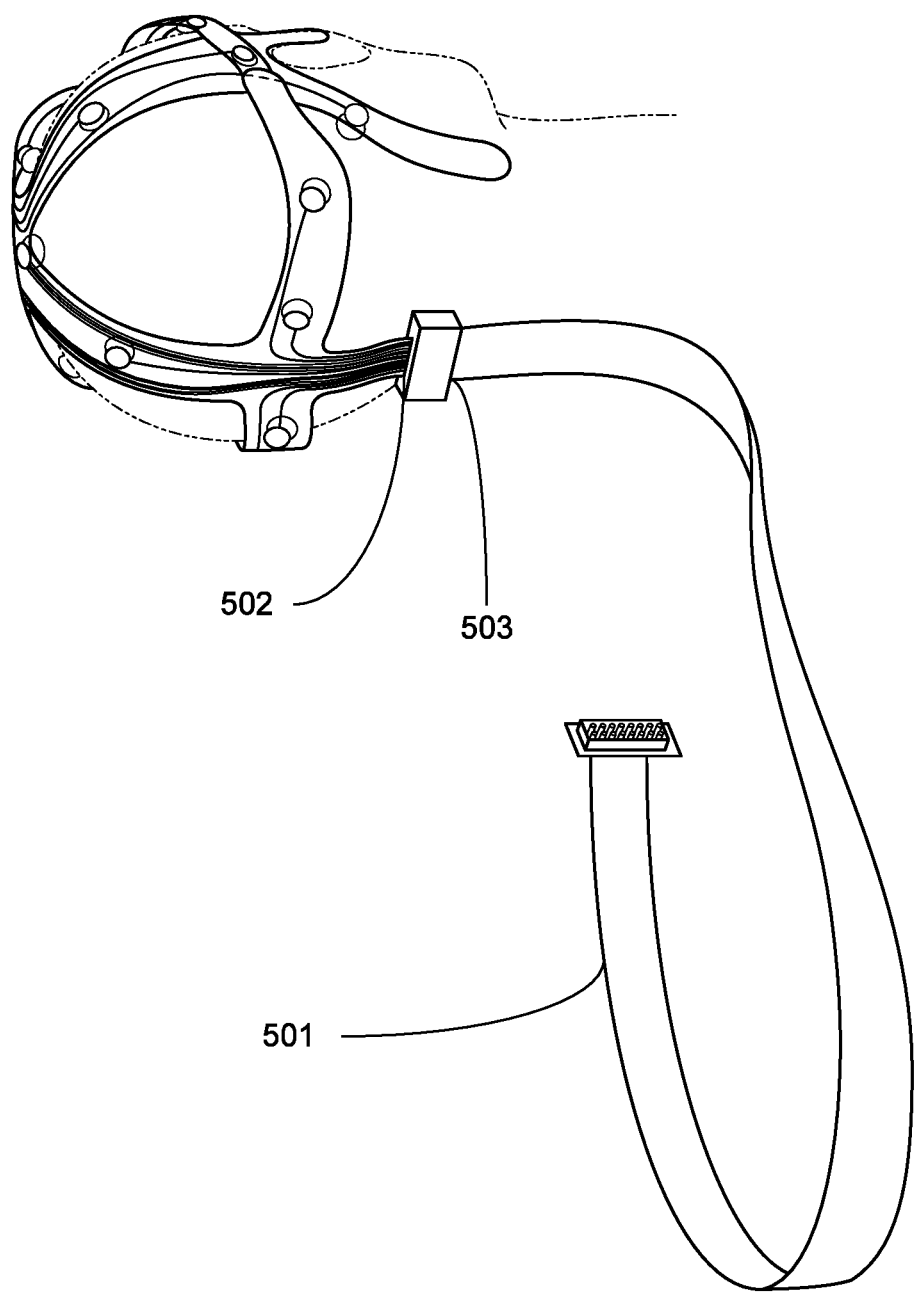
FIG. 5 depicts another perspective view of the EEG apparatus upon affixing to a human head and connected to an EEG cable.

FIG. 5 illustrates the EEG apparatus 100 affixed on a subject's head and connected to an outlet cable 130, 501. The corresponding outlet cable 130, 501 may be a transformer outlet cable. The transformer outlet cable 130, 501 may have an electrical socket contacting the connector point 119, 502 wherein conductive surfaces present on the electrical socket conductively contact printed circuitry present at the connector point 119, 502. The electrical socket may be integrated into a nonconductive clamp 503. Upon connection between the electrical socket on the outlet cable 130 and the EEG apparatus 100 at the connector point, the clamp 503 may hold the EEG apparatus connector point 119 in place, thereby facilitating the connection between the EEG apparatus 100 and the outlet cable 130, 501.

The electrode 202 may be embedded into the base layer 201 by imprint. In some embodiments, the electrode 202 may fit snuggly into the base layer 201, wherein the surface of the electrode 202 at the scalp contact point does not extend beyond the base layer 201; or it may extend by a thickness from the base layer 201. This eliminates the need for crimp or a snap-on mechanism to hold the electrodes in place. The electrode 202 may separate into two portions: the embedded portion contained within the base layer 201 and the extended portion 203 extending from the base layer. A conductive gel layer 204 may be present at the electrode 202 contact surface. The electrode 202 may be by silver—silver chloride composition. The electrode 202 thickness may be 0.005-0.030 mm, preferably at 0.015 mm.

A layer of conductive gel 204 may be present on the surface of electrodes 202. Conductive gel 204 may be potassium chloride (KCl) or hydrogel. Conductive gel 204 may be pre-applied to electrodes' 202 contact surfaces and spread for even distribution. On top of the conductive gel layer 204 may be a sponge 208 to keep the gel in place and preventing gel dry-out. Additional conductive gel 204 may be placed inside the sponge 208, such that the sponge 208 is soaked with conductive gel.

The lower surface of the EEG apparatus 100 may be covered by a holder. The cross section of the holder may be depicted in FIG. 2 as 205. This holder may hold the EEG apparatus 100 in place and also cover the entire lower surface of the EEG apparatus 100 to prevent dust gathering on the lower surface. At use time, the EEG apparatus 100 may be removed from the holder 205. The sponges 208 may be removed prior to applying the electrodes 105, 202 to the subject's scalp.

Each electrode may be in contact with the corresponding circuitry 120 and integrated into the circuitry by means of silver/silver chloride paint. Electrodes 105, 202 according to embodiments do not require additional crimps to connect with the circuitry. Electrodes 105, 202 may be integrally connected to the EEG apparatus 100 to improve comfort during application to the subject's scalp.

According to embodiments, the EEG apparatus 100 may be disposable, such that no EEG apparatus 100 may be used twice. This may prevent discomfort in attaching electrodes to subjects, and may prevent transmission of bacteria and/or virus between users.

Figure 3:
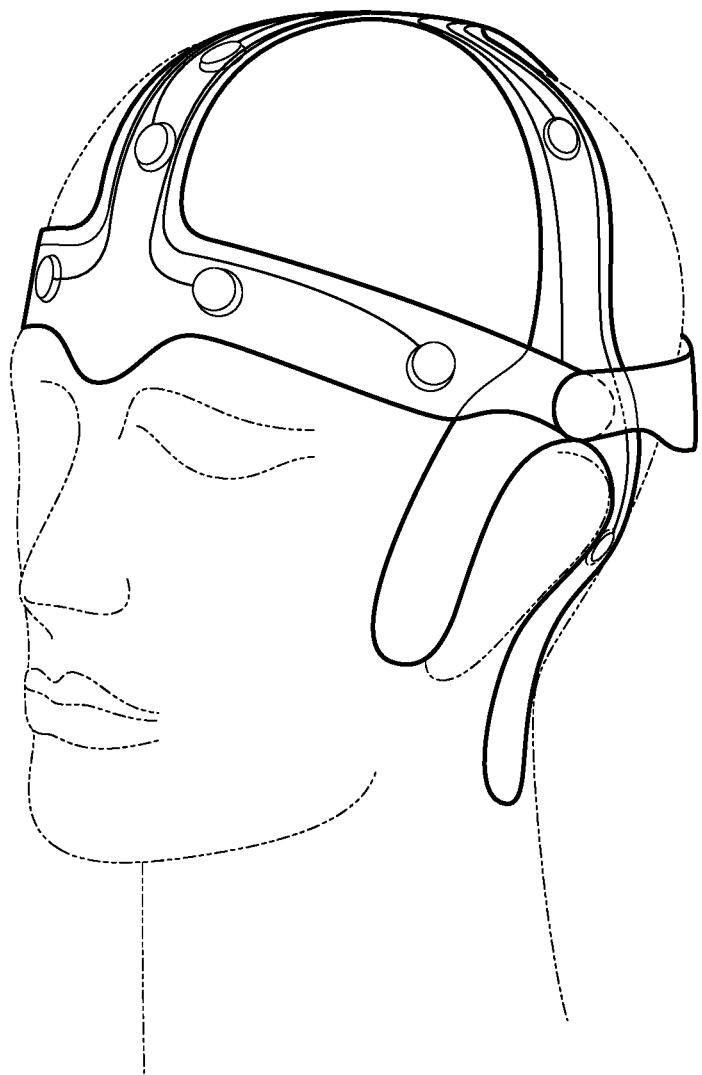
FIG. 3 depicts a perspective view of the EEG apparatus upon affixing to a human head.
Figure 4:
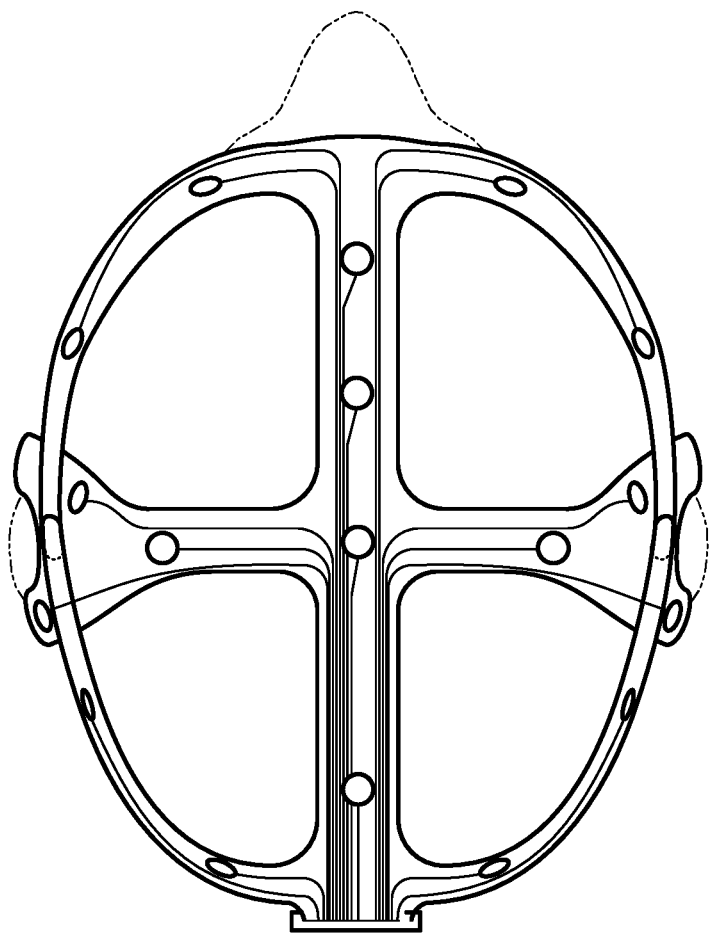
FIG. 4 depicts the top view of the EEG apparatus upon affixing to a human head.

According to other embodiments of the present invention, there is provided a method for performing electroencephalography. In embodiments, the method may comprise providing an EEG apparatus 100 according to embodiments in the present invention. Examples of this method may be shown in FIG. 3 and FIG. 4. FIG. 3 is the front perspective view of the EEG apparatus 100 as placed on the subject's head. FIG. 4 is a top perspective view showing placement of the EEG apparatus 100 of FIG. 1 on the subject's head. FIG. 5 is the lateral view showing the placement of the EEG apparatus 100 of FIG. 1 on the subject's head with the EEG apparatus 100 connected to an outside cable through the connector 119, 502.

In embodiments, a subject may be selected for EEG measurement. The subject may be suspected to or have a brain disease, such as epilepsy, stroke, or other diseases identifiable or diagnosable by EEG measurement. Human subjects without suspected or known medical conditions may also be selected for EEG measurement for other purposes, such as measuring brainwaves.

The subject's forehead may be cleaned and dried before placement of the EEG apparatus 100, such as by wiping with alcohol or water and drying by a gauze pad. The subject's hair may also be parted along the sagittal line to expose the scalp. Parting hair may be by an applicator, such as a cotton-tipped applicator.

The EEG apparatus 100 may be removed from the holder 205, exposing the lower surface of the EEG apparatus 100, wherein electrodes 105, 202 with conductive gel may be present. Sponges 208 present on the electrodes 105, 202 may be removed to expose the conductive gel layer.

The EEG apparatus 100 may be placed onto the subject's head by first peeling off the thin film covering the attachment gel spot on the forehead anchor 102. The forehead anchor 102 may be positioned at the middle of the subject's forehead, such that the anchor 102 touches the forehead near the upper region of the nose. The attachment gel may hold the forehead anchor 102 in place.

The front portion 104 of the EEG apparatus 100 may be placed by lining the front portion 104 to the subject's forehead. Conductive gel coming in contact with the subject's skin may provide attachment. Additionally, the attachment points 122, 123 at the end of each front left wing 103 and front right wing 101 may be attached to the corresponding attachment points 124, 125 located on the coronal left and right wings. The attachment points 122, 123 may be left hanging for pending attachment to the attachment points on the coronal left and right wings. The EEG apparatus 100 as shown in FIG. 1 may have electrodes present at positions $F_7$ and $F_{p1}$ on the left side wing 103 of the front portion 104, while the right side wing 101 may have electrodes present at positions $F_8$ and $F_{p2}$ upon attachment.

The front mid sheet 106 of the EEG apparatus 100 may be attached to the subject's scalp by gently compressing the front mid sheet 106 into place along the sagittal line. Electrodes 105 present on the front mid sheet 106 may attach to the scalp by conductive gel, thereby enabling EEG measurement. The EEG apparatus 100 as shown in FIG. 1 may have an electrode present at positions $F_z$ and a ground electrode along the sagittal line on the front mid sheet 106 upon attachment.

In the next step, the subject's hair may be parted along the coronal line. The coronal left side wing 113 of the coronal portion 121 may be placed from the subject's head top along the coronal line to the ear. Film cover on top of the attachment gel spots on the coronal left and right side wings 113, 112 extensions 116, 117, 114, 115 may be removed to expose the attachment gel spots. The coronal left side wing's 113 first extension 116 may be placed such that it surrounds the subject's left ear on the front side without touching the ear, while the second extension 117 may be placed such that it surrounds the subject's left ear on the back side without touching the ear. The right side wing 112 of the coronal portion 121 may be placed from the subject's head top along the coronal line to the ear. The coronal right side wing 112 second extension 114 may be placed such that it surrounds the subject's right ear on the front side without touching the ear, while the first extension 115 may be placed such that it surrounds the subject's right ear on the back side without touching the ear.

The coronal left side wing 113 upon application may have electrodes at position $C_3$, position $T_3$, and position $A_1$ on the second extension 117. The coronal right side portion 112 upon application may have electrodes at position $C_4$, position $T_4$, and position $A_2$ on the first extension 115.

Upon affixing the coronal portion 121 to the subjects' ears, the attachment points 122, 123 on the frontal portion 104 may be affixed to the attachment points 124, 125 on the coronal portion 121, respectively. The middle mid sheet 107 may then be affixed to the scalp along the sagittal line by gentle compressing. The middle mid sheet 107 electrodes may be at positions $C_z$ and $P_z$.

The lateral portion 129 of the EEG apparatus 100 may be attached to the subject's scalp by gentle compressing of the lateral portion 129 into place. The rear left side wing 111 and right side wing 110 may be compressed to the left and right side of the subject's head, respectively. Electrodes 105 present on the lateral portion 129 may attach to the scalp by conductive gel. Additionally, attachment points 126, 127 at the end of each rear left wing 111 and rear right wing 110 may be attached to the corresponding attachment points 124, 125 located on the coronal left and right wings. The EEG apparatus 100 as shown in FIG. 1 may have electrodes present at positions $T_5$ and $O_1$ on the rear left side wing 111, while the rear right side wing 110 may have electrodes present at positions $T_6$ and $O_2$ upon attachment.

The method according to embodiments may further comprise connecting the connection point 119 with a reusable EEG cable for use with an EEG measurement system according to techniques known in the art. For example, the EEG cable may be connected to a 10-20 labeled touch-proof DIN connectors at the terminal end of an EEG interface cable into an EEG head box locations.

The method may comprise using the EEG apparatus 100 to obtain EEG measurement of the subject's brain function. EEG measurement readings may be collected by the EEG measurement system.

Upon completion of EEG measurement, the EEG apparatus 100 may be removed from the subject's head. The lateral portion 129 may be removed by first removing the rear left side wing 111 then the right side wing 110 by gentle peeling. Removal may start by peeling from the attachment points 126, 127 on each side of the rear wings 110, 111, before the rear left side wing 111 and the rear right side wing 110 may be removed. The back of the sagittal portion or the rear mid sheet 108 may be removed by peeling off gently, then the middle mid sheet 107 may be peeled off.

The frontal portion 106 may be first removed by removing the front left side wing 103 and front right side wing 101 from the attachment points 124, 125 by peeling off the front attachment points 122, 123. Then gentle peeling at the forehead anchor 102, then peeling the front left side wing 103, before peeling the front right side wing 101 may be conducted. Then, peeling along the sagittal line to the coronal portion 121 may remove the front portion 106.

The coronal portion 121 may be peeled off starting at the second extension 117 on the left side wing 113, then the first extension on the left side wing 116 before the left side wing 113 may be completely peeled off. The right side wing 112 may be removed in similar manner, with the first extension 115 of the right side wing 112 being peeled off, then the second extension 114 of the right side wing 112 may be peeled off. The right side wing 112 may be completely peeled off along the coronal line. Upon removal of the EEG apparatus 100, the EEG apparatus 100 may be disposed of.

In another embodiment, there may be provided a method for treating a disease or condition which may be may be diagnosed by EEG measurement. A subject potentially having a neurological condition or disease may be selected, and EEG measurement may be performed on the subject using the EEG apparatus 100. The method may comprise measuring the subject's brainwave using the EEG apparatus 100 according to embodiments. The disease may be diagnosed by the EEG measurement results and treated by appropriate treatment means as determined by medical professionals. The disease may be epilepsy, stroke, or other brain disease diagnosable by EEG measurement.

While the present invention has been discussed in detail with reference to certain embodiments, other embodiments are possible. Therefore, the scope of the appended claims should not be limited to the description of the preferred embodiments contained in this disclosure. All references cited herein are incorporated by reference in their entirety.

What is claimed is:

1. An apparatus for electroencephalography measurement on a human subject, the apparatus comprising:
   a mid sheet extending from the forehead anchor to the connector point, comprising a plurality of embedded electrodes at positions $F_z$, $C_z$, and $P_z$ of the International Standard 10-20 System for electrode placement and a ground electrode;
   a frontal portion comprising:
      a front left wing extending from the mid sheet at the forehead anchor at an angle and comprising a plurality of embedded electrodes at positions $F_7$ and $F_{p1}$ of the International Standard 10-20 System for electrode placement and an attachment point at the distal end;
      a front right wing extending from the mid sheet at the forehead anchor at an angle and in the opposite direction of the front left wing, comprising a plurality of embedded electrodes at positions $F_8$ and $F_{p2}$ of the International Standard 10-20 System for electrode placement and an attachment point at the distal end;
      a forehead anchor between the front left wing and the front right wing; and
   a coronal portion comprising:
      a coronal left side wing extending from the middle of the mid sheet at an angle and comprising a body and two extensions, a first extension extending from the body to one side at an angle less than 90 degrees taken between the body and the first extension in the clockwise position, a second extension extending from the body to the opposite side at an angle less than 90 degrees taken between the body and the second extension in the anti-clockwise position, with embedded electrodes at positions $C_3$ and $T_3$ in the body, and an embedded electrode at position $A_1$ on the first extension, the electrode positions are according to the International Standard 10-20 System for electrode placement, and an attachment point at the distal end of the body;
      a coronal right side wing extending from the middle of the mid sheet at an angle and in the opposite direction of the front left wing, comprising a body and two extensions, a first extension extending from the body to one side at an angle less than 90 degrees taken between the body and the first extension in the clockwise position, and a second extension extending from the body to the opposite side at an angle less than 90 degrees taken between the body and the second extension in the anti-clockwise position, with embedded electrodes at positions $C_4$ and $T_4$ in the body, and an embedded electrode at position $A_2$ on the second extension, the electrode positions are according to the International Standard 10-20 System for electrode placement, and an attachment point at the distal end of the body;
   a lateral portion comprising:
      a rear left side wing extending at an angle from the rear end of the mid sheet comprising a plurality of embedded electrodes at positions $T_5$ and $O_1$ of the International Standard 10-20 System for electrode placement and an attachment point at the distal end of the rear left wing;
      a rear right side wing extending at an opposing angle from the mid sheet comprising a plurality of embedded electrodes at positions $T_6$ and $O_2$ of the International Standard 10-20 System for electrode placement and an attachment point at the distal end of the rear right wing; and
      a plurality of circuitry connecting the plurality of electrodes to a common connector point situated at the end of the mid sheet,
   wherein the attachment points comprise Velcro surfaces,
   wherein the mid sheet ends at a connector point with embedded circuitry,
   wherein the mid sheet, the frontal portion, the coronal portion, and the lateral portion comprise the apparatus body, and
   wherein the apparatus body comprises a base layer.

2. The apparatus of claim 1, wherein the base layer is transparent or seen-through.

3. The apparatus of claim 1, wherein the circuitry is printed within the apparatus.

4. The apparatus of claim 1, wherein the plurality of electrodes are imprinted silver or silver chloride electrodes.

5. The apparatus of claim 1, wherein the circuitry and the plurality of electrodes are printed in one stage.

6. The apparatus of claim 1, wherein the plurality of electrodes extend from the apparatus and are exposed outside the base layer.

7. The apparatus of claim 6, wherein the plurality of electrodes are covered with a conductive gel at surfaces exposed outside the base layer.

8. The apparatus of claim 1, further comprising sponges covering the plurality of electrodes conductive gel surface.

9. The apparatus of claim 8, wherein the sponges are soaked in conductive gel.

10. The apparatus of claim 9, further comprising a holder in which the apparatus is placed.

11. A method of performing electroencephalography on a human subject, the method comprising:
   providing an apparatus for performing electroencephalography on a human subject, the apparatus comprising:
      a mid sheet extending from the forehead anchor to the connector point, comprising a plurality of embedded electrodes at positions $F_z$, $C_z$, and $P_z$ of the International Standard 10-20 System for electrode placement and a ground electrode;
      a frontal portion comprising:
         a front left wing extending from the mid sheet at the forehead anchor at an angle and comprising a plurality of embedded electrodes at positions $F_7$ and $F_{p1}$ of the International Standard 10-20 System for electrode placement and an attachment point at the distal end;
         a front right wing extending from the mid sheet at the forehead anchor at an angle and in the opposite direction of the front left wing, comprising a plurality of embedded electrodes at positions $F_8$ and $F_{p2}$ of the International Standard 10-20 System for electrode placement and an attachment point at the distal end;

a forehead anchor between the front left wing and the front right wing; and a coronal portion comprising:

a coronal left side wing extending from the middle of the mid sheet at an angle and comprising a body and two extensions, a first extension extending from the body to one side at an angle less than 90 degrees taken between the body and the first extension in the clockwise position, a second extension extending from the body to the opposite side at an angle less than 90 degrees taken between the body and the second extension in the anti-clockwise position, with embedded electrodes at positions $C_3$ and $T_3$ in the body, and an embedded electrode at position $A_1$ on the first extension, the electrode positions are according to the International Standard 10-20 System for electrode placement, and an attachment point at the distal end of the body;

a coronal right side wing extending from the middle of the mid sheet at an angle and in the opposite direction of the front left wing, comprising a body and two extensions, a first extension extending from the body to one side at an angle less than 90 degrees taken between the body and the first extension in the clockwise position, and a second extension extending from the body to the opposite side at an angle less than 90 degrees taken between the body and the second extension in the anti-clockwise position, with embedded electrodes at positions $C_4$ and $T_4$ in the body, and an embedded electrode at position $A_2$ on the second extension, the electrode positions are according to the International Standard 10-20 System for electrode placement, and an attachment point at the distal end of the body;

a lateral portion comprising:

a rear left side wing extending at an angle from the rear end of the mid sheet comprising a plurality of embedded electrodes at positions $T_5$ and $O_1$ of the International Standard 10-20 System for electrode placement and an attachment point at the distal end of the rear left wing;

a rear right side wing extending at an opposing angle from the mid sheet comprising a plurality of embedded electrodes at positions $T_6$ and $O_2$ of the International Standard 10-20 System for electrode placement and an attachment point at the distal end of the rear right wing; and a plurality of circuitry connecting the plurality of electrodes to a common connector point situated at the end of the mid sheet, wherein the attachment points comprise Velcro surfaces, wherein the mid sheet ends at a connector point with embedded circuitry, wherein the mid sheet, the frontal portion, the coronal portion, and the lateral portion comprise the apparatus body, and wherein the apparatus body comprises a base layer;

affixing the apparatus to the patient by affixing the frontal portion to the forehead of the patient, affixing the front portion of the mid sheet from the forehead anchor to the junction between the mid sheet and the coronal elements along the sagittal line of the patient's head, affixing the coronal elements along the coronal line of the human subject's head, affixing the extensions around the left ear and right ear of the patient, securing the front left and right wings to the coronal attachment points, affixing the middle part of the mid sheet from the $C_z$ location to the junction between lateral portion and mid sheet along the sagittal line of the human subject's head, affixing the lateral portion to the human subject's scalp and securing the rear left and right wings to the coronal attachment points, affixing the rear portion of the mid sheet to the patient's scalp; and connecting the connector point to an electroencephalography cable, wherein affixing the apparatus further comprises contacting the conductive gel to adhere the electrodes to the human subject's scalp.

12. A method of diagnosing a neurological condition or disease, the method comprising:

selecting a patient potentially having a neurological condition or disease; and performing electroencephalography on the patient using the method of claim 11 to produce an electroencephalogram.

13. The method of claim 12, further comprising diagnosing the neurological condition or disease by interpreting the electroencephalogram.

14. The method of claim 13, further comprising treating the neurological condition or disease diagnosed.

15. The method of claim 14, wherein the neurological condition or disease is epilepsy.

16. The method of claim 14, wherein the neurological condition or disease is a stroke.

* * * * *